(12) United States Patent
Seibel et al.

(10) Patent No.: US 12,251,086 B2
(45) Date of Patent: Mar. 18, 2025

(54) OPTICAL FIXATION MONITOR

(71) Applicant: University of Washington, Seattle, WA (US)

(72) Inventors: Eric J. Seibel, Seattle, WA (US);
Saniel D. Lim, Brookfield, WI (US);
Mark E. Fauver, Seattle, WA (US)

(73) Assignee: University of Washington, Seattle, WA (US)

( * ) Notice: Subject to any disclaimer, the term of this patent is extended or adjusted under 35 U.S.C. 154(b) by 833 days.

(21) Appl. No.: 17/400,983

(22) Filed: Aug. 12, 2021

(65) Prior Publication Data
US 2022/0061825 A1 Mar. 3, 2022

Related U.S. Application Data

(60) Provisional application No. 63/074,445, filed on Sep. 3, 2020.

(51) Int. Cl.
*A61B 10/02* (2006.01)
*A61B 10/04* (2006.01)

(52) U.S. Cl.
CPC ...... *A61B 10/0275* (2013.01); *A61B 10/0283* (2013.01); *A61B 2010/045* (2013.01)

(58) Field of Classification Search
None
See application file for complete search history.

(56) References Cited

U.S. PATENT DOCUMENTS

| | | | |
|---|---|---|---|
| 8,867,803 B2 | 10/2014 | Seibel et al. | |
| 9,310,302 B2 | 4/2016 | Garsha et al. | |
| 2015/0185140 A1* | 7/2015 | Yazdanfar | A61B 10/0233 356/402 |
| 2016/0367228 A1* | 12/2016 | Solomon | G01N 21/17 |
| 2020/0124506 A1 | 4/2020 | Taft et al. | |

OTHER PUBLICATIONS

H. Fox, F. B. Johnson, J. Whiting, and P. P. Roller, "Formalde-hyde fixation," J. Histochem. Cytochem., vol. 33, No. 8, pp. 845-853, Aug. 1985.

M. E. Boon, P. O. Gerrits, H. E. Moorlag, P. Nieuwenhuis, and L. P. Kok, "Formaldehyde fixation and microwave irradiation," Histochem. J., vol. 20, Nos. 6-7, pp. 313-322, Jun. 1988.

(Continued)

*Primary Examiner* — Aurelie H Tu
(74) *Attorney, Agent, or Firm* — McDonnell Boehnen Hulbert & Berghoff LLP

(57) ABSTRACT

A monitoring system includes a light source, a light detector, a processor, and a non-transitory computer readable medium storing instructions that, when executed by the processor, cause the monitoring system to perform functions. The functions include illuminating, via the light source, a biological sample that is within a container while a fixation process is performed on the biological sample. The functions also include determining, via the light detector, that an optical transmittance of the biological sample satisfies a condition. The functions also include ceasing the fixation process in response to determining that the optical transmittance of the biological sample satisfies the condition.

20 Claims, 8 Drawing Sheets

MONITORING SYSTEM 100

(56) References Cited

OTHER PUBLICATIONS

R. Thavarajah, V. K. Mudimbaimannar, J. Elizabeth, U. K. Rao, and K. Ranganathan, "Chemical and physical basics of routine formaldehyde fixation," J. Oral Maxillofac. Pathol., vol. 16, No. 3, pp. 400-405, Sep./Dec. 2012.
A. C. Wolff et al., "Human epidermal growth factor receptor 2 testing in breast cancer: American society of clinical oncology/college of american pathologists clinical practice guideline focused update," Arch. Pathol. Lab Med., vol. 138, No. 2, pp. 241-256, Feb. 2014.
U. G. Sathyanarayana et al., "Determination of optimum formalin fixation duration for prostate needle biopsies for immunohistochemistry and quantum dot FISH analysis," Appl. Immunohistochem. Mol. Morphol., vol. 23, No. 5, pp. 364-373, May 2015.
J. A. Ibarra and L. W. Rogers, "Fixation time does not affect expression of HER2/neu: A pilot study," Amer. J. Clin. Pathol., vol. 134, No. 4, pp. 594-596, Oct. 2010.
V. Sujoy, M. Nadji, and A. R. Morales, "Brief formalin fixation and rapid tissue processing do not affect the sensitivity of ER immunohistochemistry of breast core biopsies," Amer. J. Clin. Pathol., vol. 141, No. 4, pp. 522-526, Apr. 2014.
A. Halilovic et al., "Brief fixation enables same-day breast cancer diagnosis with reliable assessment of hormone receptors, E-cadherin and HER2/Neu," J. Clin. Pathol., vol. 70, No. 9, pp. 781-786, Sep. 2017.
A. M. Gown, "Tweaking and nudging toward improved-IHC quality," Appl. Immunohistochem. Mol. Morphol., vol. 17, No. 5, pp. 363-365, Oct. 2009.
N. S. Goldstein, M. Ferkowicz, E. Odish, A. Mani, and F. Hastah, "Minimum formalin fixation time for consistent estrogen receptor immunohistochemical staining of invasive breast carcinoma," Amer. J. Clin. Pathol., vol. 120, No. 1, pp. 86-92, Jul. 2003.
H. Yaziji and T. Barry, "Diagnostic immunohistochemistry: What can go wrong?" Adv. Anat. Pathol., vol. 13, No. 5, pp. 238-246, Sep. 2006.
J. D. Webster, M. A. Miller, D. Dusold, and J. Ramos-Vara, "Effects of prolonged formalin fixation on diagnostic immunohistochemistry in domestic animals," J. Histochem. Cytochem., vol. 57, No. 8, pp. 753-761, Aug. 2009.
L. Agrawal, K. B. Engel, S. R. Greytak, and H. M. Moore, "Understanding preanalytical variables and their effects on clinical biomarkers of oncology and immunotherapy," Semin. Cancer Biol., vol. 52, pp. 26-38, Oct. 2018.
S. Susman et al., "The role of the pathology department in the preanalytical phase of molecular analyses," Cancer Manag. Res., vol. 10, pp. 745-753, Apr. 2018.
S. Farkona, E. P. Diamandis, and I. M. Blasutig, "Cancer immunotherapy: The beginning of the end of cancer?" BMC Med., vol. 14, No. 1, p. 73, May 2016.
K. K. Lindfors and C. J. Rosenquist, "Needle core biopsy guided with mammography: A study of cost-effectiveness," Radiology, vol. 190, No. 1, pp. 217-222, Jan. 1994.
M. J. Silverstein et al., "Image-detected breast cancer: State-of-the-art diagnosis and treatment," J. Amer. College Surgeons, vol. 209, No. 4, pp. 504-520, Oct. 2009.
M. A. Ganott et al., "Ultrasound guided core biopsy versus fine needle aspiration for evaluation of axillary lymphadenopathy in patients with breast cancer," ISRN Oncol., vol. 2014, Jan. 2014, Art. No. 703160. [Online]. Available: https://www.hindawi.com/journals/ism/2014/703160/.
S. Loeb, H. B. Carter, S. I. Berndt, W. Ricker, and E. M. Schaeffer, "Complications after prostate biopsy: Data from SEER-medicare," J. Urol., vol. 186, No. 5, pp. 1830-1834, Nov. 2011.
K. E. Calhoun and B. O. Anderson, "Needle biopsy for breast cancer diagnosis: A quality metric for breast surgical practice," J. Clinical Oncol., vol. 32, No. 21, pp. 2191-2192, 2014.

D. Chafin, A. Theiss, E. Roberts, G. Borlee, M. Otter, and G. S. Baird, "Rapid two-temperature formalin fixation," PLoS One, vol. 8, No. 1, Jan. 2013, Art. No. e54138.
I. E. Chesnick, J. T. Mason, T. J. O. Leary, and C. B. Fowler, "Elevated pressure improves the rate of formalin penetration while preserving tissue morphology," J. Cancer, vol. 1, pp. 178-183, Oct. 2010.
N. Zou et al., "Ultrasound-facilitated formalin fixation of biological specimens," Biotech. Histochem., vol. 86, No. 6, pp. 413-420, Dec. 2011.
J. P. Bulte et al., "One-day core needle biopsy in a breast clinic: 4 years experience," Breast Cancer Res. Treat., vol. 137, No. 2, pp. 609-616, Jan. 2013.
C. B. Moelans, D. Oostenrijk, M. J. Moons, and P. J. Van Diest, "Formaldehyde substitute fixatives: Effects on nucleic acid preservation," J. Clin. Pathol., vol. 64, No. 11, pp. 960-967, Nov. 2011.
F. Boissiere-Michot et al., "The non-crosslinking fixative RCL2-CS100 is compatible with both pathology diagnosis and molecular analyses," Pathol. Oncol. Res., vol. 19, No. 1, pp. 41-53, Jan. 2013.
J. Y. Chung et al., "Histomorphological and molecular assessments of the fixation times comparing formalin and ethanol-based fixatives," J. Histochem. Cytochem., vol. 66, No. 2, pp. 121-135, Feb. 2018.
C. Perry et al., "A buffered alcohol-based fixative for histomorphologic and molecular applications," J. Histochem. Cytochem., vol. 64, No. 7, pp. 425-440, Jul. 2016.
R. Das, C. W. Burfeind, G. M. Kramer, and E. J. Seibel, "Pathology in a tube: Step 1. Fixing, staining, and transporting pancreatic core biopsies in a microfluidic device for 3D imaging," Proc. SPIE, vol. 8976, Mar. 2014, Art. No. 89760R. [Online]. Available: https://www.spiedigitallibrary.org/conference-proceedings-of-spie/8976/1/Pathology-in-a-tube-Step-1-Fixing-staining-and/10.1117/12.2041106.full.
R. Das, C. W. Burfeind, S. D. Lim, S. Patle, and E. J. Seibel, "Pathology in a tube step 2: Simple rapid fabrication of curved circular cross section millifluidic channels for biopsy preparation/3D imaging towards pancreatic cancer detection and diagnosis," Proc. SPIE, vol. 10491, Feb. 2018, Art. No. 1049118. [Online]. Available: https://www.spiedigitallibrary.org/conference-proceedings-of-spie/10491/1049118/Pathology-in-a-tube-step-2-simple-rapid-fabrication/10.1117/12.2291018.full.
D. R. Bauer, B. Stevens, D. Chafin, A. P. Theiss, and M. Otter, "Active monitoring of formaldehyde diffusion into histological tissues with digital acoustic interferometry," Proc SPIE, vol. 3, No. 1, Feb. 2016, Art. No. 017002.
A. P. Sarvazyan, M. W. Urban, and J. F. Greenleaf, "Acoustic waves in medical imaging and diagnostics," Ultrasound Med. Biol., vol. 39, No. 7, pp. 1133-1146, Jul. 2013.
K. Daoudi, A.-C. Boccara, and E. Bossy, "Detection and discrimination of optical absorption and shear stiffness at depth in tissue-mimicking phantoms by transient optoelastography," Appl. Phys. Lett., vol. 94, No. 15, Apr. 2009, Art. No. 154103.
D. S. Elson, R. Li, C. Dunsby, R. Eckersley, and M.-X. Tang, "Ultrasound-mediated optical tomography: A review of current methods," Interface Focus, vol. 1, No. 4, pp. 632-648, Jun. 2011.
P.-Y. Chao and P.-C. Li, "Three-dimensional shear wave imaging based on full-field optical-sectioned laser speckle contrast imaging," in Proc. IEEE Int. Ultrason. Symp. (IUS), Oct. 2015, pp. 1-3.
T. J. Hall, M. Bilgen, M. F. Insana, and T. A. Krouskop, "Phantom materials for elastography," IEEE Trans. Ultrason., Ferroelectr., Freq. Control, vol. 44, No. 6, pp. 1355-1365, Nov. 1997.
S. J. Kirkpatrick, D. D. Duncan, and E. M. Wells-Gray, "Detrimental effects of speckle-pixel size matching in laser speckle contrast imaging," Opt. Lett., vol. 33, No. 24, pp. 2886-2888, Dec. 2008.
M. Riccio, G. Breglio, A. Irace, and P. Spirito, "An equivalent time temperature mapping system with a 320×256pixels full-frame 100 kHz sampling rate," Rev. Sci. Instrum., vol. 78, No. 10, Oct. 2007, Art. No. 106106.
C. A. Carrascal, S. Chen, A. Manduca, J. F. Greenleaf, and M. W. Urban, "Improved shear wave group velocity estimation method based on spatiotemporal peak and thresholding motion search," IEEE Trans. Ultrason., Ferroelectr., Freq. Control, vol. 64, No. 4, pp. 660-668, Apr. 2017.

(56) References Cited

OTHER PUBLICATIONS

Y. Cheng, S. Li, R. J. Eckersley, D. S. Elson, and M.-X. Tang, "Detecting tissue optical and mechanical properties with an ultrasound modulated optical imaging system in reflection detection geometry," Biomed. Opt. Express, vol. 6, No. 1, pp. 63-71, Jan. 2015.

P.-Y. Chao and P.-C. Li, "Three-dimensional shear wave imaging based on full-field laser speckle contrast imaging with one-dimensional mechanical scanning," Opt. Express, vol. 24, No. 17, pp. 18860-18871, Aug. 2016.

M. Orescanin and M. Insana, "Shear modulus estimation with vibrating needle stimulation," IEEE Trans. Ultrason., Ferroelectr., Freq. Control, vol. 57, No. 6, pp. 1358-1367, Jun. 2010.

R. K. Manapuram et al., "Estimation of shear wave velocity in gelatin phantoms utilizing PhS-SSOCT," Laser Phys., vol. 22, No. 9, pp. 1439-1444, Sep. 2012.

Y. Ling et al., "Effects of fixation and preservation on tissue elastic properties measured by quantitative optical coherence elastography (OCE)," J. Biomech., vol. 49, No. 7, pp. 1009-1015, May 2016.

M. Srinivasan and D. Sedmak, "Effect of fixatives and tissue processing on the content and integrity of nucleic acids," Amer. J. Pathol., vol. 161, No. 6, pp. 1961-1971, Dec. 2002.

B. F. Kennedy, P. Wijesinghe, and D. D. Sampson, "The emergence of optical elastography in biomedicine," Nature Photon., vol. 11, No. 4, pp. 215-221, Apr. 2017.

Ł. Ambrozinski et al., "Acoustic micro-tapping for non-contact 4D imaging of tissue elasticity," Sci. Rep., vol. 6, Dec. 2016, Art. No. 38967.

S. Anand et al., "Effects of formalin fixation on tissue optical properties of in-vitro brain samples," Proc. SPIE, vol. 9321, Mar. 2015, Art. No. 93210Z. [Online]. Available: https://www.spiedigitallibrary.org/conference-proceedings-of-spie/9321/932107/Effects-of-formalin-fixation-on-tissue-optical-properties-of-in/10.1117/12.2076961.full.

H. Zhang, D. Salo, D. M. Kim, S. Komarov, Y.-C. Tai, and M. Y. Berezin, "Penetration depth of photons in biological issues from hyperspectral imaging in shortwave infrared in transmission and reflection geometries," Proc SPIE, vol. 21, No. 12, Dec. 2016, Art. No. 126006.

C. Ash, M. Dubec, K. Donne, and T. Bashford, "Effect of wavelength and beam width on penetration in light-tissue Interaction using computational methods," Lasers Med. Sci., vol. 32, No. 8, pp. 1909-1918, Nov. 2017.

M. L. Lerch, D. R. Bauer, D. Chafin, A. Theiss, M. Otter, and G. S. Baird, "Precision medicine starts with preanalytics: Real-time assessment of tissue fixation quality by ultrasound time-of-flight analysis," Appl. Immunohistochem. Mol. Morphol., vol. 25, No. 3, pp. 160-167, Mar. 2016.

J. M. M. Cates and K. A. Troutman, "Quality management of the immuno-histochemistry laboratory: A practical guide," Appl. Immunohistochem. Mol. Morphol., vol. 23, No. 7, pp. 471-480, Aug. 2015.

M. Dietel et al., "Diagnostic procedures for non-small-cell lung cancer (NSCLC): Recommendations of the European expert group," Thorax, vol. 71, No. 2, pp. 177-184, Feb. 2016.

Lim, Saniel D, Qixuan Huang, and Eric J Seibel. "Evaluation of Formalin Fixation for Tissue Biopsies Using Shear Wave Laser Speckle Imaging System." IEEE Journal of Translational Engineering in Health and Medicine 7 (2019):1-10. [Online] Available: https://ieeexplore.ieee.org/ielx7/6221039/8579633/08684905.pdf.

\* cited by examiner

```
┌─────────────────────────────────────────────────────────────┐
│  ILLUMINATING A BIOLOGICAL SAMPLE THAT IS WITHIN A          │
│  CONTAINER WHILE A FIXATION PROCESS IS PERFORMED ON THE     │
│  BIOLOGICAL SAMPLE                                          │
└─────────────────────────────────────────────────────────────┘
   302 ↓

┌─────────────────────────────────────────────────────────────┐
│  DETERMINING THAT AN OPTICAL TRANSMITTANCE OF THE           │
│  BIOLOGICAL SAMPLE SATISFIES A CONDITION                    │
└─────────────────────────────────────────────────────────────┘
   304 ↓

┌─────────────────────────────────────────────────────────────┐
│  CEASING THE FIXATION PROCESS IN RESPONSE TO DETERMINING    │
│  THAT THE OPTICAL TRANSMITTANCE OF THE BIOLOGICAL           │
│  SAMPLE SATISFIES THE CONDITION                             │
└─────────────────────────────────────────────────────────────┘
   306
```

OPTICAL FIXATION MONITOR

CROSS REFERENCE TO RELATED APPLICATION

The present application claims priority to U.S. Provisional Application No. 63/074,445, filed on Sep. 3, 2020, the contents of which are hereby incorporated by reference.

BACKGROUND

Core needle biopsy (CNB) is a common technique for obtaining tissue samples for aiding in diagnosis and therapeutic decisions for treating various conditions such as cancer. However, the evaluation of tissues obtained via CNB can be negatively impacted by inconsistent processing prior to evaluation. For example, tissues obtained via CNB are generally immersed in formalin soon after the biopsy to preserve the tissue. However, variations in the degree of formalin fixation of the tissue that occurs during this process can cause errors in subsequent analysis of the tissue.

SUMMARY

A first example includes a method comprising: illuminating a biological sample that is within a container while a fixation process is performed on the biological sample; determining that an optical transmittance of the biological sample satisfies a condition; and ceasing the fixation process in response to determining that the optical transmittance of the biological sample satisfies the condition.

A second example includes a monitoring system comprising: a light source; a light detector; a processor; and a non-transitory computer readable medium storing instructions that, when executed by the processor, cause the monitoring system to perform functions comprising: illuminating, via the light source, a biological sample that is within a container while a fixation process is performed on the biological sample; determining, via the light detector, that an optical transmittance of the biological sample satisfies a condition; and ceasing the fixation process in response to determining that the optical transmittance of the biological sample satisfies the condition.

A third example includes a non-transitory computer readable medium storing instructions that, when executed by a monitoring system, cause the monitoring system to perform functions comprising: illuminating a biological sample that is within a container while a fixation process is performed on the biological sample; determining that an optical transmittance of the biological sample satisfies a condition; and ceasing the fixation process in response to determining that the optical transmittance of the biological sample satisfies the condition.

When the term "substantially" or "about" is used herein, it is meant that the recited characteristic, parameter, or value need not be achieved exactly, but that deviations or variations, including, for example, tolerances, measurement error, measurement accuracy limitations, and other factors known to those of skill in the art may occur in amounts that do not preclude the effect the characteristic was intended to provide. In some examples disclosed herein, "substantially" or "about" means within +/−0-5% of the recited value.

These, as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

BRIEF DESCRIPTION OF THE DRAWINGS

FIG. 8 is a block diagram of a method, according to an example.

DETAILED DESCRIPTION

As discussed above, more consistent processes for preserving tissue obtained via biopsy are needed. Such devices and methods are discussed in the present disclosure.

Within examples, a monitoring system includes a light source (e.g., a laser), a light detector (e.g., a photodiode), a processor, and a non-transitory computer readable medium storing instructions that, when executed by the processor, cause the monitoring system to perform functions. The functions include illuminating, via the light source, a biological sample (e.g., biopsied breast tissue) that is within a container while a fixation process is performed on the biological sample. For example, the biological sample is placed within a transparent container and is immersed in formalin. The formalin binds to and preserves proteins within the biological sample for subsequent evaluation. The degree to which the formalin binds to and preserves proteins within the biological sample is generally dependent on the duration the biological sample is immersed within the formalin and on the temperature of the formalin solution during that duration.

The functions also include determining, via the light detector, that an optical transmittance of the biological sample satisfies a condition. The optical transmittance of the biological sample can be used as a proxy for the degree of formalin fixation that has occurred in the biological sample. For example, the intensity of the light generated by the light source and incident upon the biological sample is compared to the intensity of the light transmitted through the container and the biological sample. Once the intensity of the transmitted light becomes less than or equal to a predetermined threshold value that corresponds with a desired level of formalin fixation, the monitoring system can responsively cease the fixation process. For example, the monitoring system can flush the formalin out of the container or cool the biological sample and/or the formalin to a temperature at which the formalin binding process substantially stops.

The monitoring system can be modular, for example, the container can be separable from the rest of the monitoring system such that the biological sample within the container can be transported and/or stored within the container prior to or after fixation of the biological sample. In some examples, the container is disposable.

Figure 1:
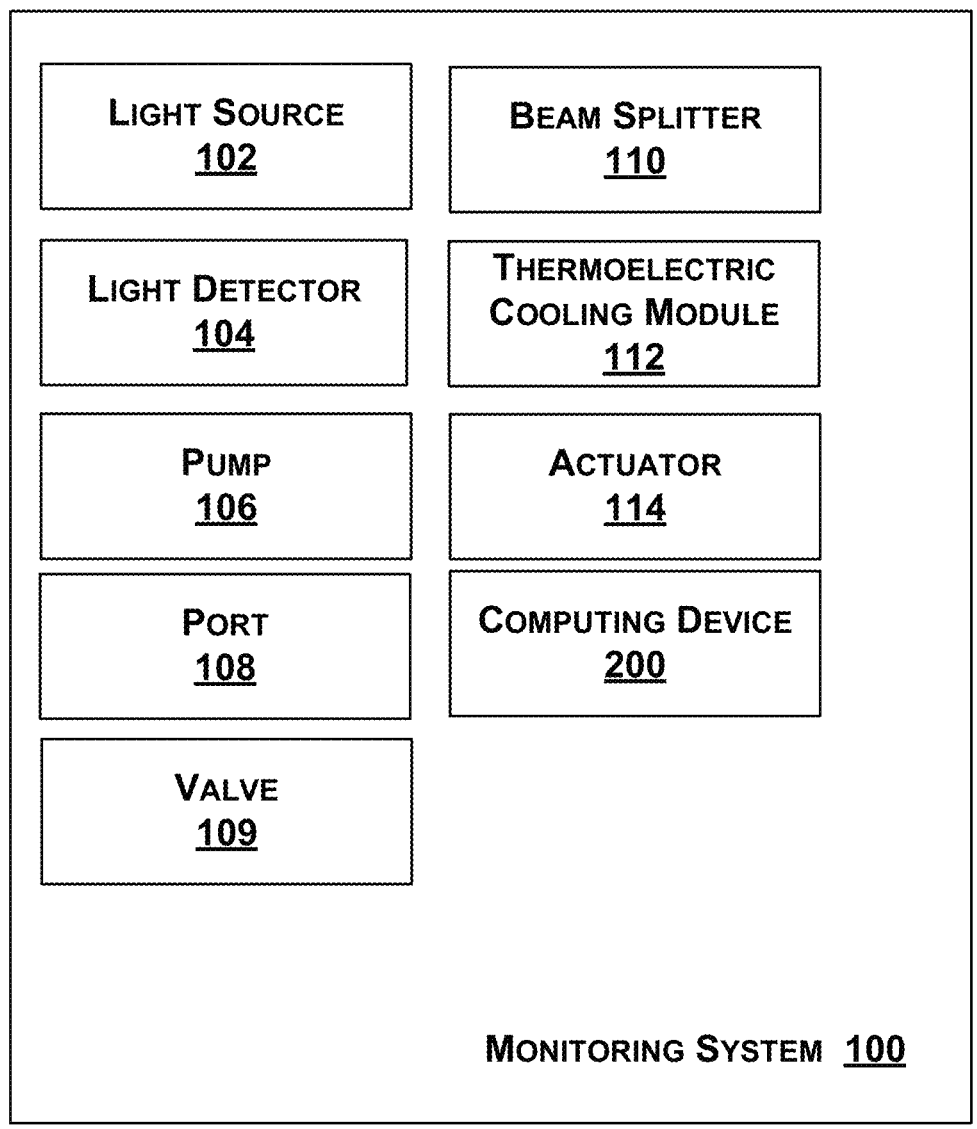
FIG. 1 is a block diagram of a monitoring system, according to an example.

FIG. 1 is a block diagram of a monitoring system 100. The monitoring system 100 includes one or more of each of the following: a light source 102, a light detector 104, a pump 106, a port 108, a beam splitter 110, a thermoelectric cooling module 112, an actuator 114, and a computing device 200.

The light source 102 can be a laser or a broadband light source such as a tungsten-halogen light source. The light source 102 could also take the form of one or more light-emitting diodes (LEDs).

The light detector 104 can be a spectrometer or a photodiode, for example. Additionally, the light detector 104 could include an array of photodiodes or an area-based image sensor (e.g., a camera). The light detector 104 generally faces the light source 102.

The pump 106 generally takes the form of a diaphragm pump, but other examples are possible. The pump 106 is configured to pump liquid to and from various chambers, containers, or reservoirs of the monitoring system 100, as described in more detail below.

The port 108 forms a fluid connection to a container that holds a biological sample. Other ports 108 form a fluid connection to reservoirs within the monitoring system 100 that hold fluids such as water, paraffin, or formalin.

The valve(s) 109 can be used in conjunction with the pump 106 and the port(s) 108 to control the direction and flow of various fluids such as water, paraffin, or formalin.

The beam splitter 110 typically takes the form of two triangular prisms adhered to each other. The discontinuity of the joined surfaces of the prisms can be used to split an incident light beam into a transmitted beam and a reflected beam (e.g., having equal intensity).

The thermoelectric cooling module 112 takes the form of a junction of two different semiconductor or metal materials having differences in free electron density inherently or due to doping. When an electric current passes through the junction, a temperature gradient is generated between the two materials, which can be used to cool nearby objects such as a biological sample.

The actuator 114 is manually or electrically operated to clasp a biological sample (e.g., from a core needle). For example, the actuator 114 takes the form of a flat plate attached to a piston. In another example, the actuator 114 takes the form of a (e.g., flexible) membrane supported by one or more stiff (e.g., metal shafts) that are electromagnetically moved to clasp or release the biological sample.

Figure 2:
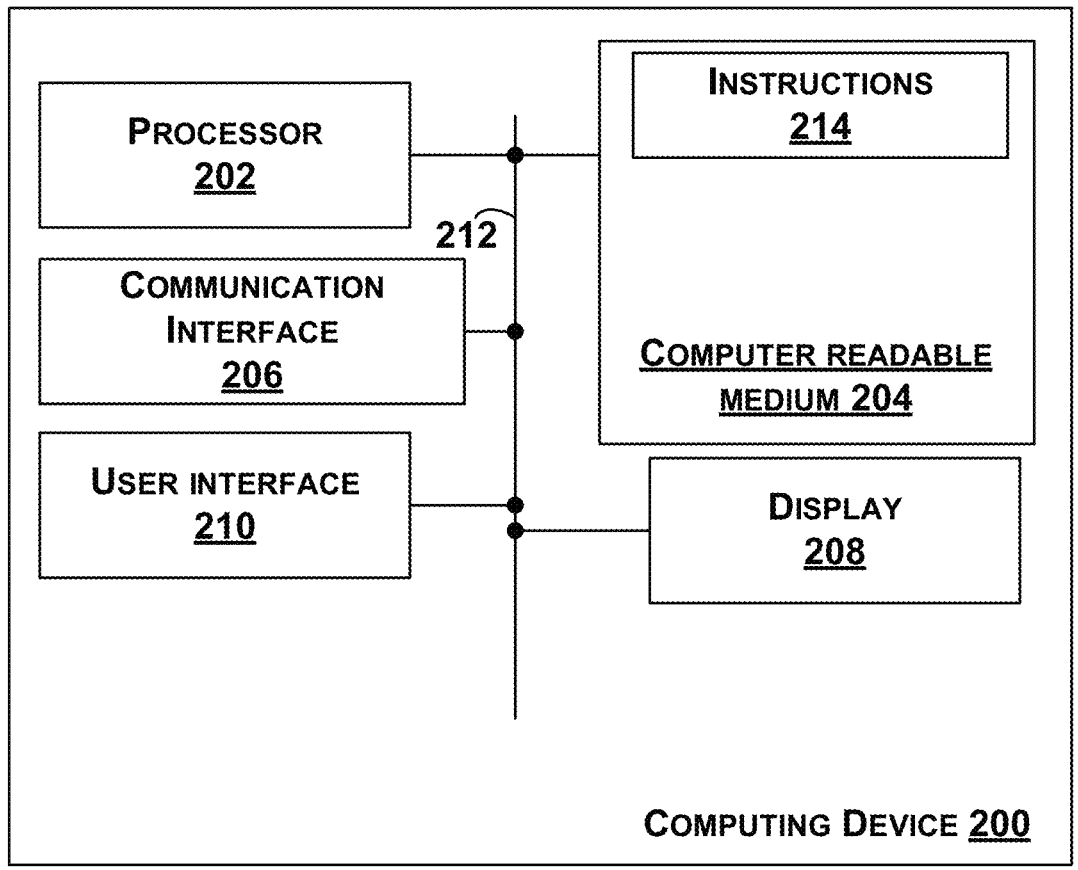
FIG. 2 is a block diagram of a computing device, according to an example.

FIG. 2 is a block diagram of the computing device 200. The computing device 200 includes one or more processors 202, a non-transitory computer readable medium 204, a communication interface 206, a display 208, and a user interface 210. Components of the computing device 200 are linked together by a system bus, network, or other connection mechanism 212.

The one or more processors 202 can be any type of processor(s), such as a microprocessor, a digital signal processor, a multicore processor, etc., coupled to the non-transitory computer readable medium 204.

The non-transitory computer readable medium 204 can be any type of memory, such as volatile memory like random access memory (RAM), dynamic random access memory (DRAM), static random access memory (SRAM), or non-volatile memory like read-only memory (ROM), flash memory, magnetic or optical disks, or compact-disc read-only memory (CD-ROM), among other devices used to store data or programs on a temporary or permanent basis.

Additionally, the non-transitory computer readable medium 204 can be configured to store instructions 214. The instructions 214 are executable by the one or more processors 202 to cause the computing device 200 to perform any of the functions or methods described herein.

The communication interface 206 can include hardware to enable communication within the computing device 200 and/or between the computing device 200 and one or more other devices. The hardware can include transmitters, receivers, and antennas, for example. The communication interface 206 can be configured to facilitate communication with one or more other devices, in accordance with one or more wired or wireless communication protocols. For example, the communication interface 206 can be configured to facilitate wireless data communication for the computing device 200 according to one or more wireless communication standards, such as one or more Institute of Electrical and Electronics Engineers (IEEE) 801.11 standards, ZigBee standards, Bluetooth standards, etc. As another example, the communication interface 206 can be configured to facilitate wired data communication with one or more other devices. The communication interface 206 can also include analog-to-digital converters (ADCs) or digital-to-analog converters (DACs) that the computing device 200 can use to control various components of the monitoring system 100.

The display 208 can be any type of display component configured to display data. As one example, the display 208 can include a touchscreen display. As another example, the display 208 can include a flat-panel display, such as a liquid-crystal display (LCD) or a light-emitting diode (LED) display.

The user interface 210 can include one or more pieces of hardware used to provide data and control signals to the computing device 200. For instance, the user interface 210 can include a mouse or a pointing device, a keyboard or a keypad, a microphone, a touchpad, or a touchscreen, among other possible types of user input devices. Generally, the user interface 210 can enable an operator to interact with a graphical user interface (GUI) provided by the computing device 200 (e.g., displayed by the display 208).

Figure 3:
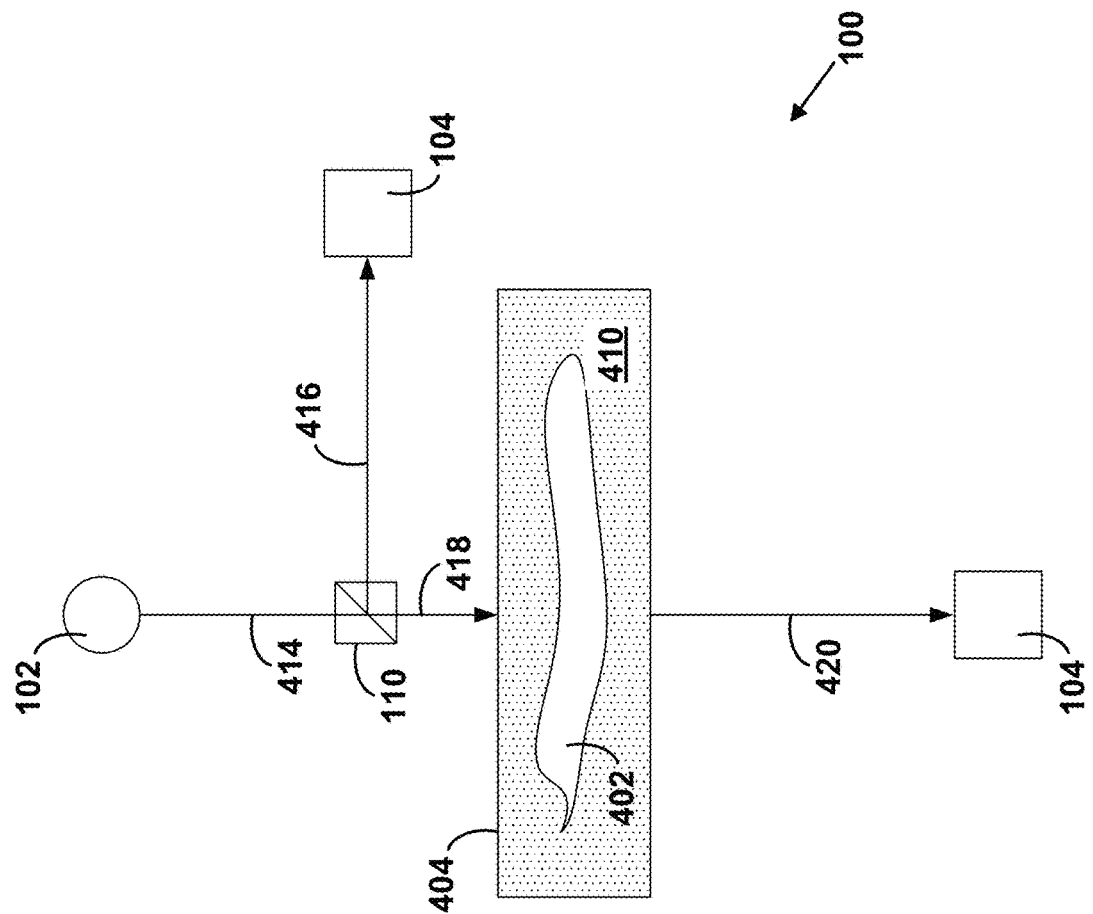
FIG. 3 is a schematic diagram of structures and functionality related to a monitoring system, according to an example.

FIG. 3 shows functionality of the monitoring system 100. A container 404 receives a biological sample 402 from a core needle or from a storage chamber within the monitoring system 100. For example, the actuator 114 (not shown in FIG. 3) can be used to clasp the biological sample 402 from the core needle as the core needle is inserted into the container 404.

In another example, the pump 106 and the port 108 (not shown in FIG. 3) can be used, via air or fluid pressure, to move the biological sample 402 from the storage chamber to the container 404 to be clasped by the actuator 114 and thereafter fixated and monitored.

The biological sample 402 is typically human tissue such as breast tissue biopsied using the core needle. The container 404 can be formed of partially or fully transparent plastic or glass. The container 404 is also fluid tight such that it is capable of additionally housing a liquid 410 (e.g., a formalin solution) that acts on the biological sample 402 to perform the fixation process. The liquid 410 is generally used as a fixative to prepare the biological sample 402 for examination. The pump 106 and/or the port 108 can be used to move the liquid 410 into the container 404 to immerse the biological sample 402 and perform the fixation process. The liquid 410 can be any liquid configured to perform the fixation process and preserve the biological sample 402.

The light source 102 illuminates the biological sample 402 that is within the container 404 (e.g., a microfluidic or a millifluidic container) while the fixation process is performed on the biological sample 402 (e.g., while the biological sample 402 is immersed within the liquid 410). For example, the light source 102 generates a light 414 and the beam splitter 110 splits the light 414 into a reference beam 416 and a sample beam 418. Thus, the biological sample 402 is illuminated with the sample beam 418 that travels through the wall of the container 404. The light 414 typically includes wavelengths ranging from 750 nm to 1000 nm, for example 800 nm to 816 nm, 792 nm to 824 nm, or a single wavelength approximately equal to 808 nm. However, the light 414 can include any wavelengths that are ultraviolet, visible, and/or infrared (e.g., near infrared).

Next, the monitoring system 100 (e.g., continuously) determines an optical transmittance of the biological sample 402 as the fixation process progresses. In practice, the optical transmittance will be a property of the container 404 and the liquid 410 as well, but the optical transmittance of the container 404 and the liquid 410 will generally not change over time. Generally, the optical transmittance of the biological sample 402 will decrease as the fixation process progresses, after an initial increase in the optical transmittance of the biological sample 402. The monitoring system 100 determines the optical transmittance of the biological sample 402 by comparing a first intensity of a portion 420 of the sample beam 418 that transmits through the biological sample 402, the liquid 410, and the container 404 to a second intensity of the reference beam 416. The optical transmittance of the biological sample 402 is generally equal to the (e.g., time varying) first intensity of the portion 420 divided by the (e.g., time varying) second intensity of the reference beam 416.

Figure 4:
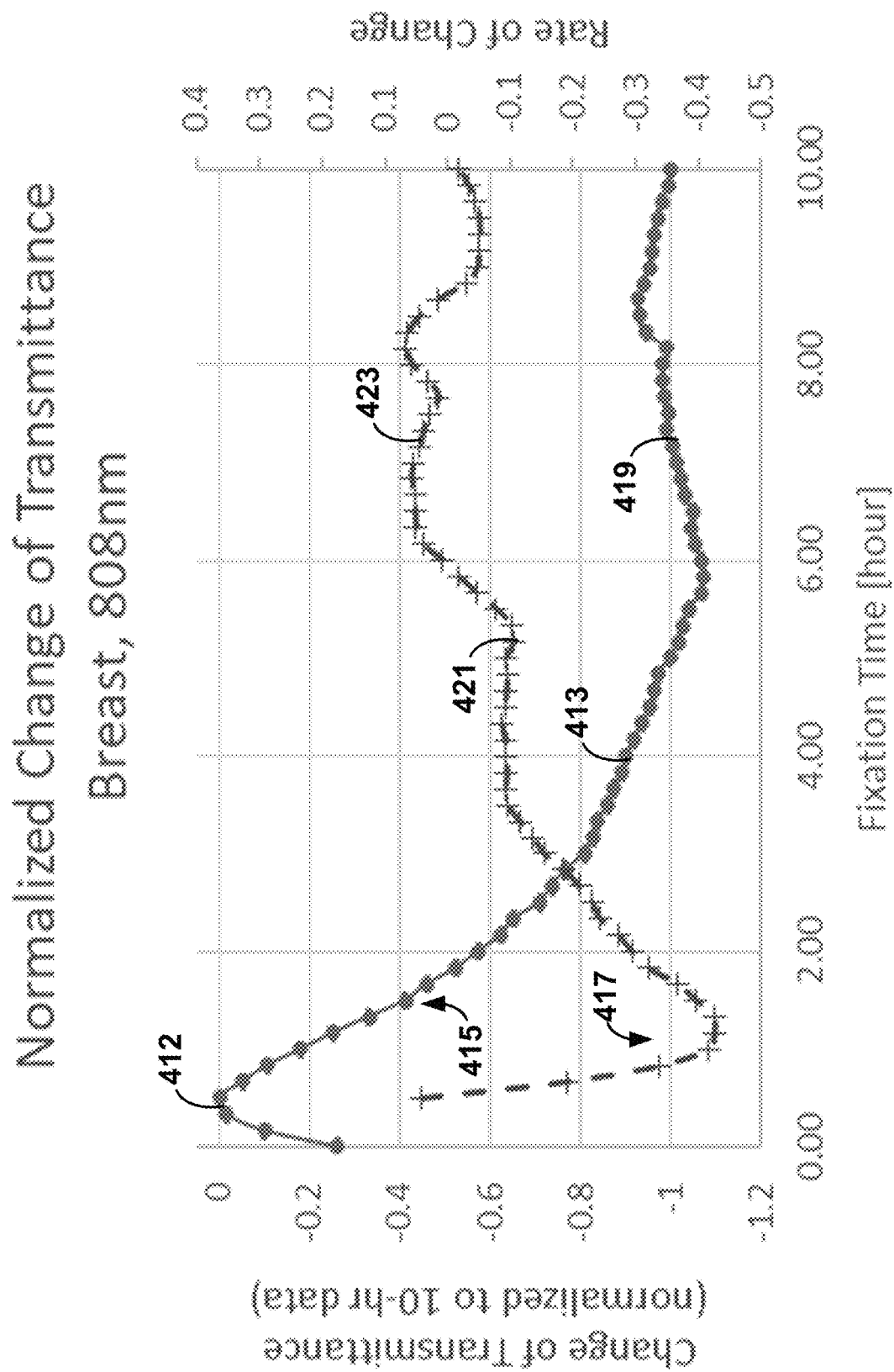
FIG. 4 is a graph of an optical transmittance of a biological sample over time during a fixation process, according to an example.

FIG. 4 shows example data 415 that depicts the transmittance of the biological sample 402 (e.g., human breast tissue) with respect to fixation time and shows example data 417 that depicts the rate of change of the transmittance with respect to fixation time. The data 415 corresponds to the vertical axis on the left and the data 417 corresponds to the vertical axis on the right.

The monitoring system 100 determines that the optical transmittance of the biological sample 402 satisfies a condition. More specifically, the monitoring system 100 determines that the optical transmittance of the biological sample 402 is less than a threshold value 413 after some time passes (e.g., after four hours of fixation). More specifically, the monitoring system 100 determines that the optical transmittance attained a maximum 412 and determines that the optical transmittance of the biological sample 402 became less than the threshold value 413 after the optical transmittance attained the maximum 412. In some examples, the fixation process causes the transmittance of the biological sample 402 to exhibit an increase prior to the transmittance exhibiting a larger decrease, as shown in FIG. 4.

The threshold value 413 can be defined in various ways. FIG. 4 shows the threshold value 413 corresponding to a transmittance that is 10% of the maximum 412 (e.g., a 90% decrease relative to the maximum 412). In other examples, threshold levels of 15%, 5%, or 1% could be used as the threshold value 413.

In other examples, the threshold value can correspond to the transmittance at which the rate of change 417 has remained within a predetermined range of values for a predetermined amount of time. For example, the monitoring system 100 can identify the threshold value 419 based on the threshold value 419 corresponding to the value 423 on the rate of change curve 417. As such, the predetermined amount of time in this example would be the amount of time that passes between the value 421 and the value 423 (e.g., approximately 2 hours) and the predetermined range of rate of change would be −0.1 to 0.1. Other examples are possible.

The monitoring system 100 then ceases the fixation process in response to determining that the optical transmittance of the biological sample 402 satisfies the condition (e.g., that the optical transmittance of the biological sample 402 is less than the threshold value 413). For example, the monitoring system 100, via the pump 106 and the port 108, remove the liquid 410 from the container 404 by flushing the container with aqueous or preserving solution.

Figure 5:
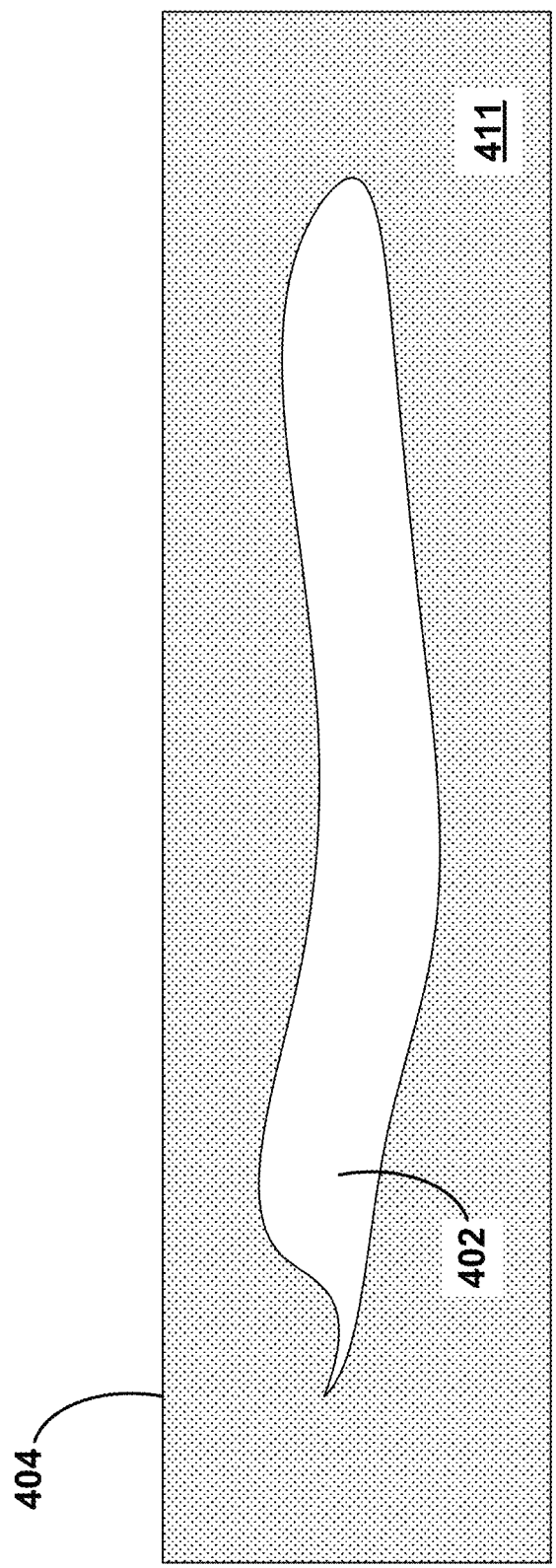
FIG. 5 is a schematic diagram of structures and functionality related to a monitoring system, according to an example.

Referring to FIG. 5, the biological sample 402 can be embedded within paraffin 411 for storage and/or cooled to a temperature that is less than or equal to 4° C., via the thermoelectric cooling module 112. The container 404 is generally sealed after ceasing the fixation process.

In some examples, the monitoring system 100 includes multiple light sources 102 with multiple corresponding light detectors 104 configured for monitoring fixation of multiple biologic samples 402 simultaneously.

Figure 6:
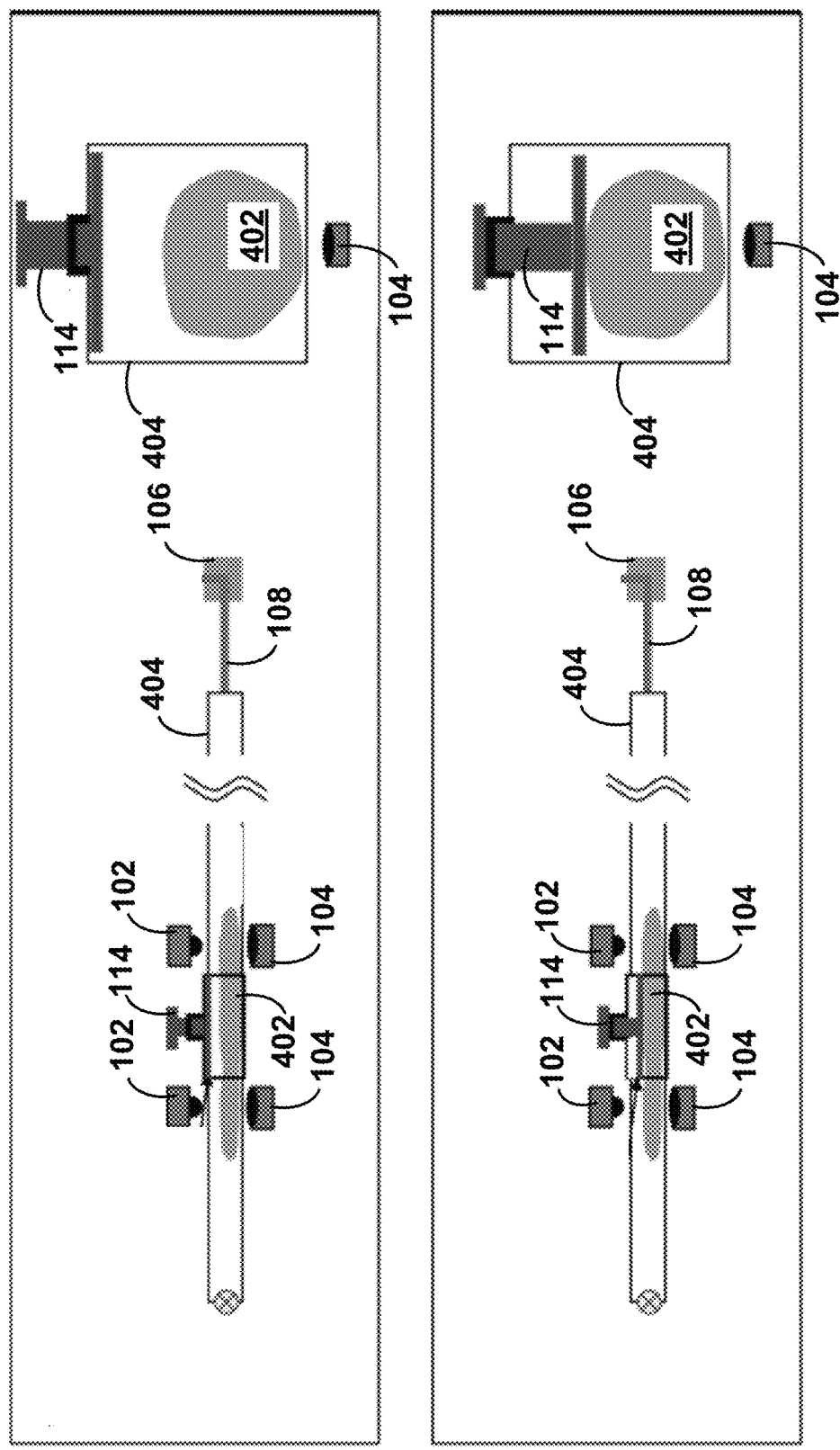
FIG. 6 is a schematic diagram of structures and functionality related to a monitoring system, according to an example.

The upper panel of FIG. 6 shows the container 404 after receiving the biological sample 402 but before the actuator 114 has clasped the biological sample 402. The lower panel of FIG. 6 shows the container 404 after the actuator 114 has clasped the biological sample 402. In FIG. 6, the actuator 114 is manually or electrically operated to clasp the biological sample 402. For example, the actuator 114 takes the form of a flat plate attached to a piston.

Figure 7:
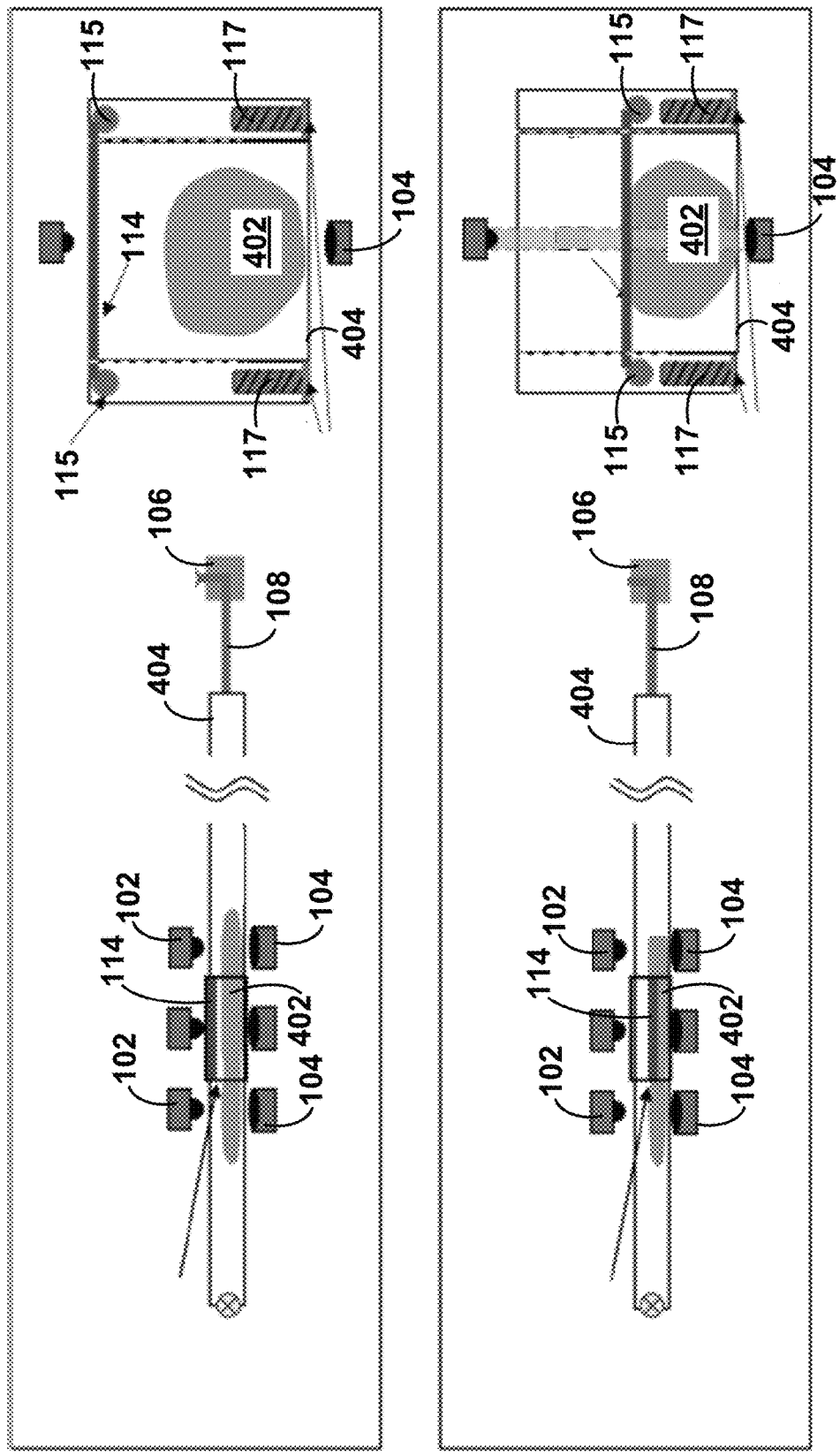
FIG. 7 is a schematic diagram of structures and functionality related to a monitoring system, according to an example.

The upper panel of FIG. 7 shows the container 404 after receiving the biological sample 402 but before the actuator 114 has clasped the biological sample 402. The lower panel of FIG. 7 shows the container 404 after the actuator 114 has clasped the biological sample 402. In FIG. 7, the actuator 114 takes the form of a membrane supported by one or more stiff (e.g., metal) shafts 115 that are electromagnetically moved to clasp or release the biological sample 402 via solenoids 117. In some examples, the membrane is flexible and conformable to the biological sample 102.

Although FIG. 6 and FIG. 7 show the light sources 102 and the light detectors 104 being oriented to emit and detect the light 414 as it travels vertically with respect to FIG. 6 and FIG. 7, the light sources 102 and the light detectors 104 can be re-oriented to detect the light 414 as it travels into or out of the page with respect to FIG. 6 and FIG. 7. In this orientation, the light sources 102 and the light detectors 104 can be positioned adjacent to the actuator 114 without the actuator 114 interfering with the light 414.

FIG. 8 is a block diagram of a method 700. As shown in FIG. 8, the method 700 includes one or more operations, functions, or actions as illustrated by blocks 302, 304, and 306. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 302, the method 300 includes illuminating the biological sample 402 that is within the container 404 while a fixation process is performed on the biological sample 402. More details regarding block 302 can be found above with reference to FIG. 3.

At block 304, the method 300 includes determining that the optical transmittance of the biological sample 402 satisfies a condition. More details regarding block 304 can be found above with reference to FIG. 4.

At block 306, the method 300 includes ceasing the fixation process in response to determining that the optical transmittance of the biological sample 402 satisfies the condition. More details regarding block 304 can be found above with reference to FIG. 5.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

What is claimed is:

1. A method comprising:
illuminating, via a light source, a biological sample that is within a container while a fixation process is performed on the biological sample;
determining, via a light detector, that an optical transmittance of the biological sample satisfies a condition; and
ceasing the fixation process in response to determining that the optical transmittance of the biological sample satisfies the condition.

2. The method of claim 1, further comprising moving a liquid into the container to initiate the fixation process, wherein the liquid is configured to preserve the biological sample.

3. The method of claim 2, wherein ceasing the fixation process comprises flushing the liquid from the container.

4. The method of claim 1, wherein determining that the optical transmittance of the biological sample satisfies the condition comprises determining that the optical transmittance of the biological sample is less than a threshold value.

5. The method of claim 1, wherein determining that the optical transmittance of the biological sample satisfies the condition comprises:
determining that the optical transmittance reached a maximum; and
determining that the optical transmittance of the biological sample became less than a threshold value after the optical transmittance reached the maximum.

6. The method of claim 1, further comprising sealing the container after ceasing the fixation process.

7. The method of claim 1, wherein ceasing the fixation process comprises embedding the biological sample in paraffin.

8. The method of claim 1, further comprising:
generating a light and splitting the light into a reference beam and a sample beam;
illuminating the biological sample with the sample beam; and
determining the optical transmittance of the biological sample by comparing a first intensity of a portion of the sample beam that transmits through the biological sample to a second intensity of the reference beam.

9. The method of claim 1, wherein ceasing the fixation process comprises cooling the biological sample to a temperature that is less than or equal to 4° C.

10. The method of claim 1, wherein illuminating the biological sample comprises illuminating the biological sample with light having wavelengths within a range of 750 nm to 1000 nm.

11. The method of claim 1, wherein the fixation process comprises immersion of the biological sample within a liquid configured to preserve the biological sample.

12. The method of claim 1, wherein ceasing the fixation process comprises ceasing the fixation process via a pump or a thermoelectric cooling module.

13. A monitoring system comprising:
a light source;
a light detector;
a processor; and
a non-transitory computer readable medium storing instructions that, when executed by the processor, cause the monitoring system to perform functions comprising:
illuminating, via the light source, a biological sample that is within a container while a fixation process is performed on the biological sample;
determining, via the light detector, that an optical transmittance of the biological sample satisfies a condition; and
ceasing the fixation process in response to determining that the optical transmittance of the biological sample satisfies the condition.

14. The monitoring system of claim 13, further comprising a pump, the functions further comprising moving a liquid into the container to initiate the fixation process via the pump.

15. The monitoring system of claim 13, further comprising a port, the functions further comprising initiating the fixation process by flowing a liquid into the container via the port.

16. The monitoring system of claim 13, wherein the light source and the light detector are configured to face each other across the container.

17. The monitoring system of claim 13, further comprising a beam splitter, the functions further comprising splitting a light generated by the light source into a sample beam and a reference beam, wherein illuminating the biological sample comprises illuminating the biological sample with the sample beam, and wherein determining that the optical transmittance of the biological sample satisfies the condition comprises comparing a first intensity of a portion of the sample beam that transmits through the biological sample to a second intensity of the reference beam.

18. The monitoring system of claim 13, the monitoring system further comprising a second light source and a second light detector, the functions further comprising:
illuminating, via the second light source, a second biological sample that is within a second container while a second fixation process is performed on the second biological sample;
determining, via the second light detector, that a second optical transmittance of the second biological sample satisfies the condition; and
ceasing the second fixation process in response to determining that the second optical transmittance of the second biological sample satisfies the condition.

19. The monitoring system of claim 13, further comprising an actuator configured to clasp the biological sample.

20. A non-transitory computer readable medium storing instructions that, when executed by a monitoring system, cause the monitoring system to perform functions comprising:
illuminating, via a light source, a biological sample that is within a container while a fixation process is performed on the biological sample;
determining, via a light detector, that an optical transmittance of the biological sample satisfies a condition; and ceasing the fixation process in response to determining that the optical transmittance of the biological sample satisfies the condition.

\* \* \* \* \*